United States Patent
Kim et al.

(10) Patent No.: US 8,119,679 B2
(45) Date of Patent: Feb. 21, 2012

(54) METHOD FOR PREPARATION OF 2,4-DINITROIMIDAZOLE WHICH IS AN INTERMEDIATE FOR INSENSITIVE MELTCASTABLE MOLECULAR EXPLOSIVE

(75) Inventors: Jin Seuk Kim, Daejeon (KR); Seung Hee Kim, Daejeon (KR); Jin Rae Cho, Daejeon (KR); Eun Mee Goh, Daejeon (KR)

(73) Assignee: Agency for Defense Development, Daejeon (KR)

( * ) Notice: Subject to any disclaimer, the term of this patent is extended or adjusted under 35 U.S.C. 154(b) by 0 days.

(21) Appl. No.: 13/042,698

(22) Filed: Mar. 8, 2011

(65) Prior Publication Data

US 2011/0275830 A1    Nov. 10, 2011

(30) Foreign Application Priority Data

May 4, 2010   (KR) .......................... 10-2010-0041972

(51) Int. Cl.
*A61K 31/4168*   (2006.01)
*C07D 233/91*   (2006.01)

(52) U.S. Cl. ................... 514/398; 548/327.1; 548/327.5
(58) Field of Classification Search ............... 548/327.1, 548/327.5; 514/398
See application file for complete search history.

(56) References Cited

U.S. PATENT DOCUMENTS 5,387,297 A * 2/1995 Damavarapu et al. ..... 149/109.6

OTHER PUBLICATIONS

Bracuti, A.J., "Crystal Structure of 2,4-dinitroimidazole (24DNI)", Journal of Chemical Crystallography, 1995, pp. 625-627, vol. 25, No. 10, Plenum Publishing Corporation, USA.

* cited by examiner

*Primary Examiner* — Kamal Saeed
*Assistant Examiner* — Janet L Coppins
(74) *Attorney, Agent, or Firm* — Pearne & Gordon LLP

(57) ABSTRACT

The present invention provides a method for preparing 2,4-dinitroimidazole, wherein separation of 1,4-donitroimidazole in powder form is avoided so that it is possible to eliminate allergy problems in workers and simplify the process, thereby improving process economy.

2 Claims, No Drawings

METHOD FOR PREPARATION OF 2,4-DINITROIMIDAZOLE WHICH IS AN INTERMEDIATE FOR INSENSITIVE MELTCASTABLE MOLECULAR EXPLOSIVE

FIELD OF THE INVENTION

The present invention relates to a method for preparing 2,4-dinitroimidazole, an intermediate product obtained during the insensitive meltcastable molecular explosive preparation process, specifically to a method for preparing 2,4-dinitroimidazole, wherein separation of 1,4-dinitroimidazole in powder form is avoided so that it is possible to eliminate allergy problems in workers and simplify the process, thereby improving process economy.

BACKGROUND OF THE INVENTION

Recently, 1-methyl-2,4,5-trinitroimidazole has drawn attention as the most promising insensitive meltcastable molecular explosive. In a conventional process, 1-methyl-2,4,5-trinitroimidazole is produced starting from 4-nitroimidazole, via preparation steps of 1,4-dinitroimidazole in a fine powder form and then 2,4-dinitroimidazole in a fine powder form.

In the above preparation method, every intermediate product obtained at the completion of each step should be provided in a fine powder form, by removing water using a desiccant and then evaporating the solvent thoroughly for drying. Therefore, such conventional method has disadvantages such as serious allergy problems often occurring in workers and process complexity.

SUMMARY OF THE INVENTION

With a purpose to solve the problems of the prior arts, the present invention has been developed to provide a method for preparing 2,4-dinitroimidazole which can dissolve allergy problems in workers, and simplify the process.

DETAILED DESCRIPTION OF THE INVENTION

The method for preparing 2,4-dinitroimidazole according to the present invention is characterized by comprising the following steps:
(1) preparing a methylene chloride solution containing 1,4-dinitroimidazole by synthesizing 1,4-dinitroimidazole by reacting 4-nitroimidazole with acetic acid and nitric acid, extracting the resulted 1,4-dinitroimidazole with methylene chloride, and removing water therefrom by using a desiccant; and
(2) adding chlorobenzene to the methylene chloride solution containing 1,4-dinitroimidazole obtained from the above step (1), allowing them to react at 120-140° C. for 4-5 hours, thereby resulting in 2,4-dinitroimidazole.

In the above step (1), the reaction of 4-nitroimidazole with acetic acid and nitric acid for nitrification may be carried out by a conventional reaction process, however it can be preferably carried out by sequentially adding nitric acid and then anhydrous acetic acid dropwise to 4-nitroimidazole for reaction, cooling, extracting and drying the mixture.

When filtering and drying 1,4-dinitroimidazole obtained by such ordinary nitrification for separation, as in a conventional process, 1,4-dinitroimidazole takes the form of a powder which may cause serious allergies in workers. For reducing such allergy problems, the present invention extracts the synthesized 1,4-dinitroimidazole immediately with methylene chloride, and then removes water from the extract so as to obtain a methylene chloride solution containing 1,4-dinitroimidazole.

For removing water in the above step (1), a desiccant may be used without specific limitation, and preferably used may be for example, magnesium sulfate, calcium sulfate, calcium chloride or sodium chloride, and more preferably magnesium sulfate.

The above step (2) in the method according to the present invention, which is for rearrangement of the nitro group of 1,4-dinitroimidazole, is carried out by adding chlorobenzene to the methylene chloride solution containing 1,4-dinitroimidazole obtained from the step (1), and being allowed to stand for reaction at 120-140° C. for 4-5 hours.

During the step (2), methylene chloride is completely evaporated by increasing the temperature to 120-140° C.

By the steps (1) and (2) of the method according to the present invention, it is possible to apply 1,4-dinitroimidazole in a solution form to the subsequent step without separating it in the form of a powder as in conventional methods, thereby dissolving allergy problems in workers, and to simplify the synthetic process for 2,4-dinitroimidazole by eliminating such separation step, thereby improving process economy.

EFFECT OF THE INVENTION

According to the method for preparing 2,4-dinitroimidazole of the present invention, it is possible to dissolve allergy problems in workers by applying the intermediate reaction products in a solution form to the subsequent steps, without separating the intermediate reaction products as a powder form, and to improve process convenience and economy by the simplified process.

PREFERRED EMBODIMENT OF THE INVENTION

Hereinafter, the present invention is further described in detail by way of the following example and comparative example, however the scope of the present invention is by no means restricted by the example which only has an illustrative purpose.

COMPARATIVE EXAMPLE

Synthesis of 1,4-dinitroimidazole 430 mL of acetic acid and 188 g of 4-nitroimidazole were charged into a 2 L-volume reactor and stirred. While stirring the mixture, 100% nitric acid(137 mL) was slowly added dropwise to the mixture at the reaction temperature of 35° C. Anhydrous acetic acid(318 mL) was added dropwise thereto at 25° C. over 1 hour. After stirring the reaction mixture at 25° C. for 2 days, the resultant was poured into 3 kg of ice cubes to obtain 1,4-dinitroimidazole as white precipitates. Then the precipitates, still cool, were immediately filtered out, washed with cold water so as to remove the residual acid, and then dried, resulting in 178.6 g(68% yield) of 1,4-dinitroimidazole in a fine white powder form. The structure of the resulted 1,4-dinitroimidazole was determined by NMR analysis, $^1$H-NMR and $^{13}$C-NMR. The results are shown below:

$^1$H-NMR (dimethyl sulfoxide-d6): δ(ppm) 8.97 (s, 1H, C2H), 9.40 (s, 1H, C5H), 13C-NMR (dimethyl sulfoxide-d6) δ(ppm) 115.9 (C5), 132.6 (C2), 144.3(C4).

Synthesis of 2,4-dinitroimidazole

The resulted 1,4-dinitroimidazole(75.0 g, 0.19 mole) in the form of white powder was placed into a 2 L-volume reactor, and thereto 600 mL of chlorobenzene was added. The mixture was refluxed at 130° C. for 4 hours. The resultant was cooled down to 25° C. to obtain 2,4-dinitroimidazole. The resultant was filtered to obtain a white powder, which was vacuum-dried to result in 70.5 g (94% yield) of 2,4-dinitroimidazole as a fine white powder. The structure of the resulted 2,4-dinitroimidazole was determined by NMR analysis, $^1$H-NMR and $^{13}$C-NMR. The results are shown below:

$^1$H-NMR (dimethyl sulfoxide-d6): δ(ppm) 8.56 (s, 1H, C5H), 10.24 (br, 1H, NH), 13C-NMR (dimethyl sulfoxide-d6): δ(ppm) 123.0 (C5), 144.0 (C2), 145.0(C4).

EXAMPLE

Synthesis of 1,4-dinitroimidazole 430 mL of acetic acid and 188 g of 4-nitroimidazole were charged into a 2 L-volume reactor and stirred. While stirring the mixture, 100% nitric acid(137 mL) was slowly added dropwise to the mixture at the reaction temperature of 35° C. Anhydrous acetic acid(318 mL) was added dropwise thereto at 25° C. over 1 hour. After stirring the reaction mixture at 25° C. for 2 days, 1,4-dinitroimidazole was synthesized. Then, the resultant was poured in 2 L cold water, and extracted three times with 500 mL of methyl chloride for each time. The obtained methylene chloride solution was dried over MgSO$_4$ so as to completely remove the water therefrom, resulting in methylene chloride extract solution containing 1,4-dinitroimidazole. The structure of the obtained 1,4-dinitroimidazole was as same as that of the comparative example.

Synthesis of 2,4-dinitroimidazole

The resulted methylene chloride solution containing 1,4-dinitroimidazole was placed into a 2 L-volume reactor, and thereto 600 mL of chlorobenzene was added. The mixture was refluxed at 130° C. for 4 hours. During the reflux, the extract solvent, methylene chloride was completely evaporated, thus resulting in 2,4-dinitroimidazole(about 80% yield). The structure of the resulted 2,4-dinitroimidazole was the same as that of the comparative example.

As illustrated above, it can be known that allergy problems in workers can be dissolved since the example uses the intermediate reaction product 1,4-dinitroimidazole in a solution form for the subsequent step, without separating it in the form of a white powder, and the process is simple and economical.

What is claimed is:
1. A method for preparing 2,4-dinitroimidazole comprising the following steps:
    (1) preparing a methylene chloride solution containing 1,4-dinitroimidazole by synthesizing 1,4-dinitroimidazole by reacting 4-nitroimidazole with acetic acid and nitric acid, extracting the resulted 1,4-dinitroimidazole with methylene chloride, and removing water therefrom by using a desiccant;
    (2) adding chlorobenzene to the methylene chloride solution containing 1,4-dinitroimidazole obtained from the above step (1), allowing them to react at 120-140° C. for 4-5 hours, thereby resulting in 2,4-dinitroimidazole.
2. The method for preparing 2,4-dinitroimidazole according to claim 1, wherein the desiccant used in the above step (1) is at least one selected from the group consisting of magnesium sulfate, calcium sulfate, calcium chloride and sodium sulfate.

* * * * *